United States Patent [19]

Yamashita et al.

[11] 4,350,149
[45] Sep. 21, 1982

[54] ENDOSCOPE AND ILLUMINATION OPTICAL SYSTEM THEREFOR

[75] Inventors: Nobuo Yamashita, Tama; Miwako Maeda, Hino, both of Japan

[73] Assignee: Olympus Optical Co., Ltd., Japan

[21] Appl. No.: 56,299

[22] Filed: Jul. 10, 1979

[30] Foreign Application Priority Data

Oct. 27, 1978 [JP] Japan .................... 53-132980

[51] Int. Cl.³ .............................. A61B 1/06
[52] U.S. Cl. ....................................... 128/6
[58] Field of Search ..................... 128/4–8, 128/22, 23; 350/96.26, 199, 442, 444; 362/299, 32, 301, 327, 346

[56] References Cited

U.S. PATENT DOCUMENTS

| 693,088 | 2/1962 | Wadsworth | 362/346 |
| 1,286,287 | 12/1918 | Glenn | 128/23 |
| 1,571,779 | 2/1926 | Allen | 362/346 |
| 2,705,490 | 4/1955 | Littmann | 128/6 |
| 2,843,112 | 7/1958 | Miller | 350/96.26 |
| 2,932,294 | 4/1960 | Fourestier et al. | 128/6 |
| 3,090,379 | 5/1963 | Ferris et al. | 128/23 |
| 3,417,745 | 12/1968 | Sheldon | 128/6 |
| 3,664,730 | 5/1972 | Cardona | 350/96.26 |
| 3,818,902 | 6/1974 | Kinoshita et al. | 128/6 |
| 3,880,148 | 4/1975 | Kanehira et al. | 128/6 |

FOREIGN PATENT DOCUMENTS

| 275901 | 10/1913 | Fed. Rep. of Germany | 128/23 |
| 588398 | 5/1925 | France | 362/346 |
| 46-54618 | of 1971 | Japan . | |
| 1121606 | 7/1968 | United Kingdom | 350/96.26 |

Primary Examiner—Robert W. Michell
Assistant Examiner—Daniel P. Burke
Attorney, Agent, or Firm—Ostrolenk, Faber, Gerb & Soffen

[57] ABSTRACT

An illumination optical system for use in an endoscope comprises a glass pane disposed in front of a source of illuminating light and which is centrally defined with a reflecting surface which is inclined with respect to the optical axis of the source. Light passing through the source in alignment with the optical axis thereof illuminates a near object while light passing through the source offset from its optical axis illuminates a far object.

17 Claims, 12 Drawing Figures

F I G. 5
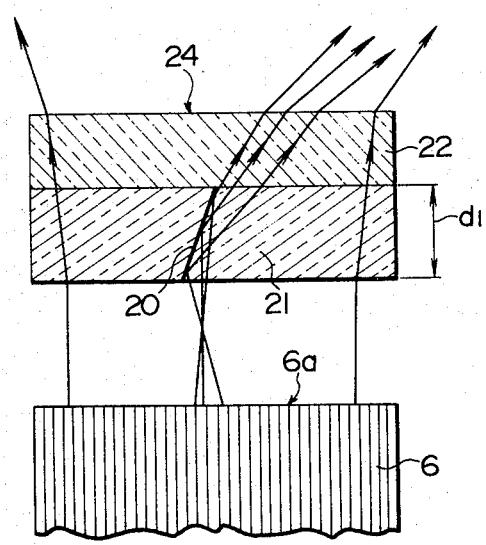

ENDOSCOPE AND ILLUMINATION OPTICAL SYSTEM THEREFOR

BACKGROUND OF THE INVENTION

The invention relates to an illumination optical system for endoscopes, and more particularly, to a system which is adapted to provide a uniform illumination to both near and far objects for purpose of observation by an endoscope.

Endoscopic diagnosis has become increasingly important in the early detection of cancers such as those which are found in the stomach. An endoscope which is used for such medical diagnosis is illustrated in FIG. 1 where its distal end 1 adapted to be inserted into coeloma is shown. A cover glass 2 is disposed in the end face of distal end 1 for passing light from an illumination optical system in order to illuminate an effected area within the coeloma. Another cover glass 3 is also disposed in the end face and is associated with an observation optical system which is used to observe an affected area that is illuminated by the light emitted through cover glass 2. In addition, channels 4, 5 are shown disposed in the end face to permit an access of forceps, for example, that is used to treat the affected area.

Referring to FIG. 2, light guide 6 is shown to be disposed adjacent cover glass 2 and is contained within the distal end of the endoscope. Light guide 6 has its end face 6a disposed close to cover glass 2 so that the illuminating light which is emitted from end face 6a passes through the latter. Image guide 7 is disposed parallel to light guide 6 within the distal end, and has its end face 7a located in opposing relationship with cover glass 3 with observation lens 8 interposed therebetween. Observation lens 8 is movable between cover glass 3 and image guide 7 for purpose of focus adjustment.

During the observation of a coeloma with an endoscope, it is sometimes necessary to observe the entire situation including an affected area and its surrounding regions, by placing the distal end of the endoscope at a distance from the affected area which is to be observed. At other times, it is also necessary to bring the distal end of the endoscope into close proximity to the affected area so that an enlarged image of the affected area or a desired limited region can be obtained. In normal use, the distal end of the endoscope is continually moved close to or away from the affected area while the diagnostician is observing the affected area. In these situations, it is undesirable for the image to vary as a function of the distance between the distal end of the endoscope and an affected area, which is illustrated in FIG. 2 by far object 11 and near object 12. Rather the illumination system should provide a uniform, high level illumination covering both far and near located objects. However, with a conventional endoscope which involves a parallax between the observation and the illumination system, it will be seen that when distal end 1 is brought into proximity to near object 12 such that observation cover glass 3 almost contacts an area P12 of object 12 which is to be observed, as shown in FIG. 2, the presence of cover glass 3 which is located opposite to area P12 prevents enough light from reaching such area to assure an accurate observation.

To overcome the difficulty which results from the parallax, it has been proposed to dispose concave lens 9 (FIG. 3) between the end face 6a of light guide 6 and cover glass 2 to permit a diffusion of light emitted by the end face 6a so that enough light can be projected to area P12 if cover glasses 2, 3 are located close to near object 12.

However, with the illumination optical system illustrated in FIG. 3, when the distal end of the endoscope is brought to a position remote from the object to illuminate an increased area, the amount of light reaching far object 11 will be substantially reduced. Consequently, the arrangement which attempted to provide a uniform illumination of far object 11 and near object 12 resulted in a minimized illumination of far object 11 at this position of the distal end of the endoscope, rendering the observation difficult.

As indicated in broken lines in FIG. 3, when the light which passes through the central region of concave lens 9 illuminates a marginal area Q12 surrounding an area P12 to be observed, and which is located opposite cover glass 2, the mirror action of the surface of marginal area Q12 reflects the light, causing it to impinge on the observation optical system through cover glass 3. Such impinging light will be reflected as by the inner surface of frame 10 associated with lens 8, to be incident on end face 7a of image guide 7, creating a ghost. The light which impinges in this manner will be repeatedly reflected in an intricate manner between lens 8 and frame 10 before it reaches the eyes of an observer through image guide 7, producing a flared field of sight, and preventing a normal observation. In particular, when concave lens 9 is used to provide a wide angle of illumination as illustrated in FIG. 3, a relatively intense light which passes through the central region of guide light 6 and illuminates the marginal area Q12 of the close object 12 will produce, by reflection, a ghost having a brightness level which is substantially greater than that of light which passes through the marginal region of light guide 6 and strongly refracted by concave lens 9 to impinge on area P12 to be observed of the same object 12. This means that an image being observed which is of a reduced level is superimposed with a flare of higher brightness. This is a disadvantage since it renders the observation of the image particularly difficult.

To overcome the described disadvantage which results from the use of concave lens 9 shown in FIG. 3, there has been proposed a different arrangement shown in FIG. 4 in which a second illumination optical system is provided which comprises second cover glass 13 disposed at a different angle from that of cover glass 2, and second light guide 14 having its end face 14a disposed close to cover glass 13 for supplying an illuminating light thereto in order to provide a satisfactory illumination of area P12 of the near object 12, which is particularly susceptible to the influence of the parallax. This arrangement enables a uniform illumination of an increased level for both far object 11 and near object 12, overcoming the described disadvantage. However, because the pair of illumination systems must be used for purpose of illumination, it becomes necessary to increase the thickness of the distal end of the endoscope which is to be inserted into the coeloma. Since it is otherwise preferable to form the distal end of the endoscope with a reduced thickness, this solution is not entirely satisfactory. An additional drawback of this arrangement is that it increases the number of parts, resulting in a complex structure and added adjustment difficulty.

SUMMARY OF THE INVENTION

It is an object of the present invention to overcome above disadvantages by providing an illumination optical system for use in an endoscope which includes a reflecting surface and a refracting surface located in front of a source of illuminating light to project an illuminating light to an area of a near object which is greatly influenced by the parallax, thereby covering an extensive field of sight including both far and near objects with a uniform and sufficient illumination.

In accordance with the invention, when a near object is to be observed, the reflecting surface projects an illuminating light to a region located in front of an observation window, thus achieving a bright illumination without an adverse influence of the parallax. A far object can also be illuminated with a sufficient brightness without any reduction in the amount of light being projected, thus assuring a satisfactory illumination which is achieved independently from the distance to an object being observed. Because an area being observed is illuminated with a greater brightness than the marginal areas, no ghost is caused by light reflected from the marginal area, making it possible to form a sharp image. As a consequence, the present invention provides an illumination optical system which is simple in construction, reduces the number of parts used, and does not require an increased diameter of the distal end of an endoscope.

BRIEF DESCRIPTION OF THE DRAWINGS

FIG. 5 is a schematic, enlarged cross section of an illumination optical system for endoscope which is constructed in accordance with one embodiment of the invention;

DESCRIPTION OF PREFERRED EMBODIMENTS

Figure 1:
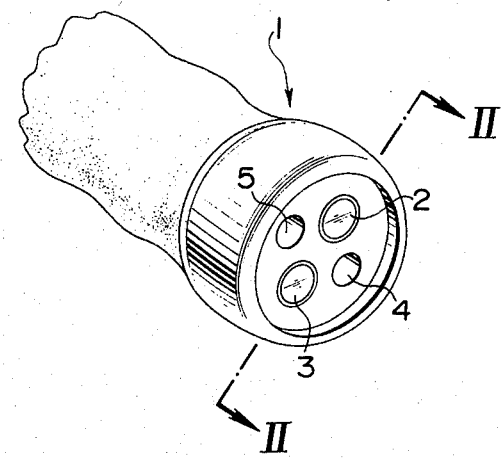
FIG. 1 is an enlarged perspective view of a distal end of an endoscope which is adapted to be inserted into coeloma.
Figure 2:
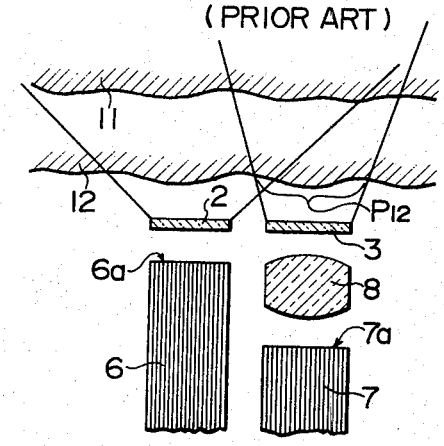
FIG. 2 is a schematic, enlarged cross section of optical systems used in an endoscope, taken along the line II—II shown in FIG. 1, illustrating a conventional arrangement.
Figure 3:
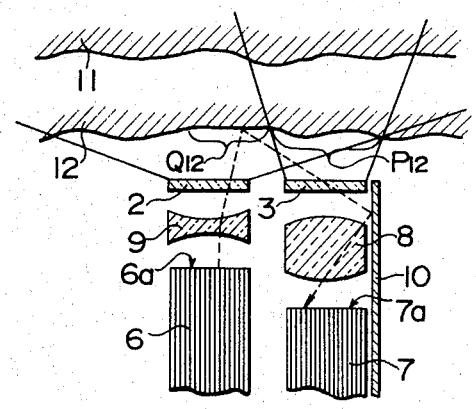
FIG. 3 is a similar view showing another arrangement of conventional optical systems.
Figure 4:
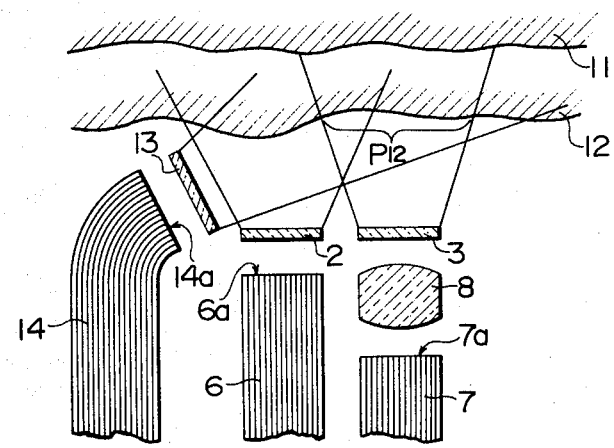
FIG. 4 is a similar view of a further example of conventional optical systems.
Figure 6:
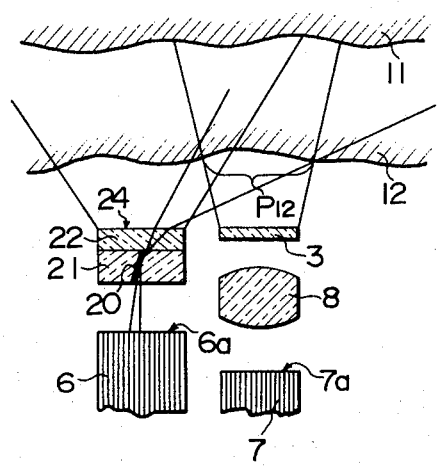
FIG. 6 is a schematic cross section of an endoscope which employs the illumination optical system shown in FIG. 5.

Referring to FIGS. 5 and 6, there is shown light guide 6 having end face 6a from which an illuminating light is emitted. Glass pane 21 having a reflecting surface 20 formed therein is disposed close to end face 6a in parallel relationship therewith. The reflecting surface 20 is formed at an angle with respect to the optical axis which is aligned with the central axis of light guide 6. It will be seen that reflecting surface 20 will receive an illuminating light having the maximum brightness level, and is oriented to project such light toward object 12 located in front of observation cover glass 3. Another glass pane 22 forming a cover glass which defines an illumination window is disposed in close contact with the upper surface of glass pane 21. The close contact between glass panes 21 and 22 causes the upper surface of glass pane 22 to act as light emitting surface to a surrounding air space, thus providing a refracting surface 24. The provision of glass pane 22 is not essential, and when it is omitted, the upper surface of glass pane 21 provides a refracting surface.

When near object 12 is illuminated with this optical system, the light which is emitted by end face 6a in the region of the optical axis, and therefore having the maximum brightness level, impinges on glass pane 21. Part of this incident light is reflected by reflecting surface 20 which is defined within glass pane 21. Reflected light then impinges glass pane 22 and passes therethrough to be refracted by refracting surface 24, defined as a boundary between glass pane 22 and the surrounding air space, to be directed toward and to illuminate area P12 of near object 12 which is located opposite to observation window 3. In this manner, a relatively intense illuminating light is used to illuminate area P12 of near object 12.

Light which passes through a region of light guide 6 offset from its central axis passes through glass panes 21 and 22 without impinging on reflecting surface 20. After passing through refracting surface 24, the light illuminates an extensive area centered about glass pane 22, covering both far object 11 and near object 12. In this manner the total field of sight including both far object 11 and near object 12 are illuminated with a sufficient brightness. In particular, area P12 of near object 12 can be illuminated without an adverse influence of parallax.

Figure 12:
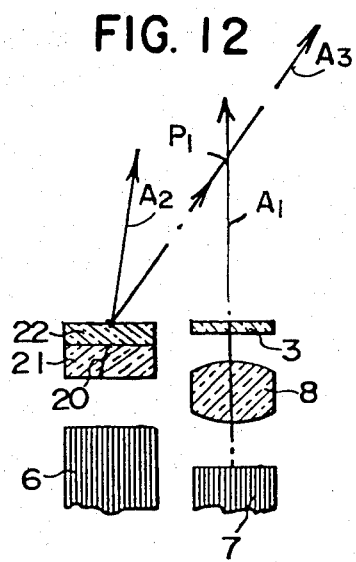
FIG. 12 is a schematic cross-section, similar to that of FIG. 6, of an endoscope which employs the illumination optical system shown in FIG. 5 and which schematically illustrates the optical axes of the various light paths of the optical system shown in FIG. 5.

The foregoing relationship between the observation and illumination optical system of FIG. 6 can also be defined in terms of the optical axes of these systems. Referring to FIG. 12, the first illumination optical axis, defined by panes 21,22, but independent of reflecting surface 20, has an effective optical axis A2 which is oblique to the observation optical axis A1 and crosses A1 at a point (not shown) beyond point $P_1$. The light associated with this axis serves to illuminate primarily distant objects as shown in FIG. 6. A second illumination optical axis A3 of the illumination optical system defined by panes 21, 22 and reflecting surface 20 is oblique to the observation optical axis A1 and crosses the axis A1 at a first point P1 located in front of the glass 3 at a location closer to the glass 3 than the point (not shown) at which axis A2 crosses axis A1. This light serves primarily to illuminate close objects as indicated at P12 of FIG. 6.

Figure 7:
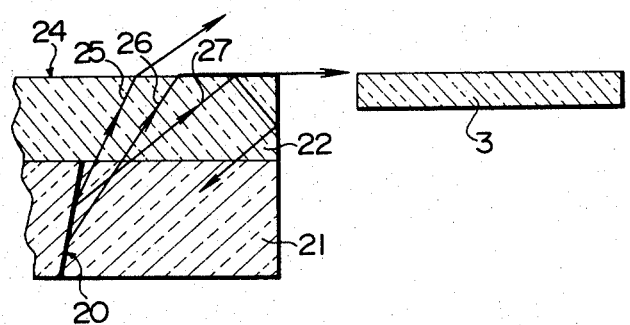
FIG. 7 is a schematic illustration of the light emitted by the illumination optical system of FIG. 6.

Referring to FIG. 7, it will be seen that the light which passes through the central region of light guide 6 in parallel relationship with the optical axis thereof will be reflected by reflecting surface 20 upon incidence thereon with a relatively large angle of reflection to produce reflected light 25 which is then refracted so as to be directed toward area P12. The light which passes through light guide 6 off its central axis will be reflected by reflecting surface 20 in a manner to produce reflected light 26 or 27 which will then be refracted by refracting surface 24 to produce an output light following a path extending parallel to refracting surface 24. Alternatively, it may be subject to a total reflection thereby reflecting internally without being emitted from refracting surface 24. Consequently, it will be understood that only that fraction of the light reflected by reflecting surface 20 which is directed toward area P12 being observed can enter the observation optical system.

As mentioned previously, it is possible for the surface of an object being observed to act like a mirror, causing illuminating light to be directly reflected into an observation optical system. If reflecting surface 20 is disposed offset from the optical axis of light guide 6, a relatively intense illuminating light which passes through the central axis of light guide 6 may be directly reflected into the observation optical system, with the result that the intensity of light which is directly reflected into the observation optical system is greater than that of light utilized for observation, thus precluding a normal observation. However, in accordance with the invention, reflecting surface 20 is positioned to cover the illuminating light which passes through the central axis of light guide 6 as mentioned above, allowing such intense light to illuminate near object 12. Consequently, if light which is directly reflected by object 12 impinges on the observation optical system, a satisfactory observation is assured by the relatively high level of the light being utilized for observation. It is to be noted that in this instance, the emitted light which passed through the central axis of light guide 6 is directed to a region in front of cover glass 3 in order to illuminate area P12 of near object 12. Far object 11 is illuminated by light which passed through light guide 6 offset from its axis and through glass panes 21, 22 without being reflected by reflecting surface 20. As a result, the illuminating light which impinges on far object 11 will exhibit a flat orientation response, providing a uniform illumination of far object 11 throughout the entire region from its center to its marginal areas, thus contributing to the ease of observation.

Figure 8:
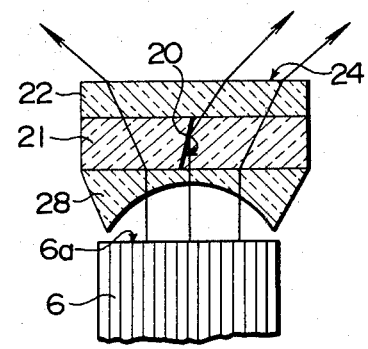
FIG. 8 is an enlarged cross section of an illumination optical system according to another embodiment of the invention.

FIG. 8 shows another embodiment of the invention in which concave lens 28 is disposed between end face 6a of light guide 6 and glass pane 21 in close contact with the latter. In this embodiment, the illuminating light which passes through the center of light guide 6 passes through the central region of concave lens 28 before it is reflected by reflecting surface 20, and thence passes through glass pane 22 to be refracted by refracting surface 24 so as to be directed toward area P12 of near object 12 in the same manner as in the embodiment shown in FIGS. 5 and 6. Illuminating light which passes through light guide 6 offset from its central axis is refracted outwardly by concave lens 28, further increasing the angle with which the illuminating light upon far objects is spread. Such a lens 28 may also be used in connection with the embodiments of the invention illustrated in FIGS. 9 and 10.

Figure 9:
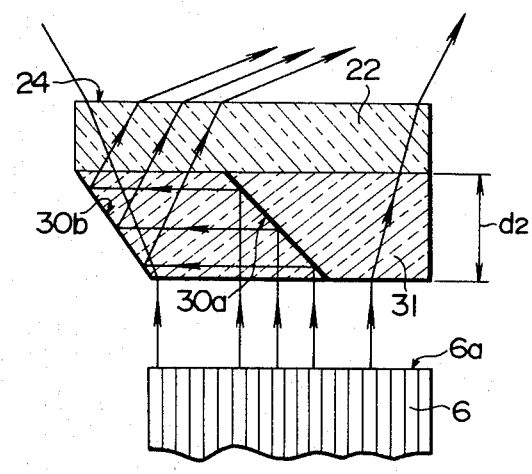
FIG. 9 is an enlarged cross section of an illumination optical system according to a further embodiment of the invention.

FIG. 9 shows a further embodiment of the invention in which a pair of reflecting surfaces are provided. In the embodiment shown in FIGS. 5 and 6, the angle of inclination of reflecting surface 20 with respect to the optical axis is chosen small since near objects 12 could not otherwise be properly illuminated. For this reason, it is necessary to increase the thickness $d_1$ of glass pane 21 to cause more of emitted light from light guide 6 to impinge on reflecting surface 20 in order to produce a sufficient amount of illuminating light. In consideration of this, in the embodiment shown in FIG. 9, glass pane 31 which is located in opposing relationship with end face 6a of light guide 6 is formed with first reflecting surface 30a and second reflecting surface 30b. First reflecting surface 30a is located in substantial alignment with the central axis of light guide 6, and is formed to have a relatively large angle of inclination with respect to the optical axis, which is about 45° in the example shown. Second reflecting surface 30b is defined by a lateral side face of glass pane 31 and forms an angle with first reflecting surface 30a. Another glass pane 22 is disposed in close contact with the upper surface of glass pane 31, in the same manner as shown in FIG. 5.

Illuminating light which passes through the central region of light guide 6 impinges on and is reflected by first reflecting surface 30a and directed toward second reflecting surface 30b within glass pane 31. The second reflecting surface 30b reflects the incident light to cause it to pass through glass panes 31 and 22 in an oblique direction. The light is then refracted by refracting surface 24 to be projected to a region located in front of cover glass 3 (see FIG. 6), thus illuminating area P12 of near object 12 (see FIG. 6).

When the thickness $d_2$ of glass pane 31 is chosen equal to the thickness $d_1$ of glass pane 21 shown in the previous embodiment, the relatively large angle of inclination of first reflecting surface 30a with respect to the optical axis of the incident light causes the thickness $d_2$ of glass pane 31 to be covered by a greater area of end face 6a of light guide 6, whereby the amount of light incident on first reflecting surface 30a increases as compared with reflecting surface 20 of previous embodiments. Thus, the illumination given to near object 12 can be increased with this embodiment.

Figure 11:
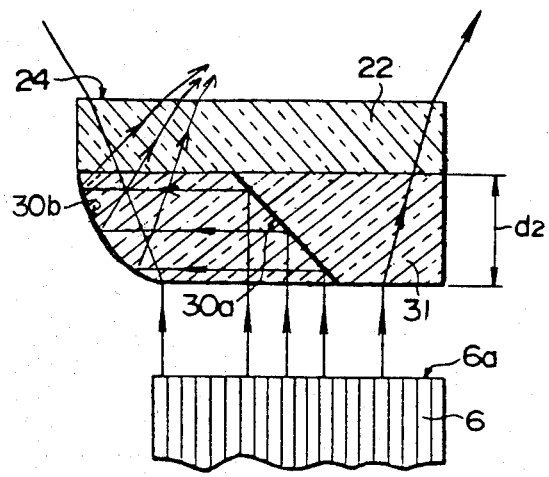
FIG. 11 is an enlarged cross-section of an illuminating optical system according to another embodiment of the present invention.

While second reflecting surface 30b is shown to lie in a plane in the embodiment shown in FIG. 9, it may be formed to provide a semi-conical reflecting surface. (See FIG. 11) Such conical surface provides a light condensing action, which may be preferred when it is desired to observe area P12 of near object 12 (see FIG. 6) with an increased local brightness level.

Figure 10:
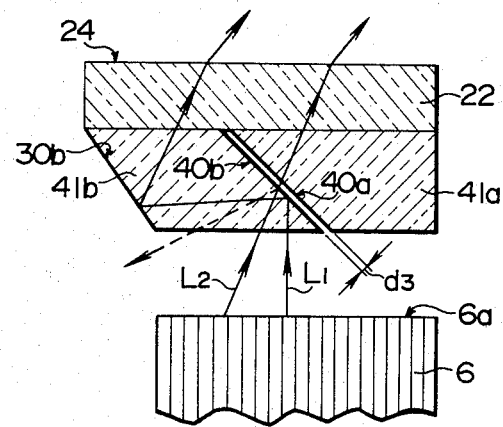
FIG. 10 is an enlarged cross section of an illumination optical system, illustrating an additional embodiment of the invention.

FIG. 10 shows an additional embodiment of the invention in which first reflecting surface 30a shown in FIG. 9 is replaced by a reflecting surface that is defined by differing refractive indices of glass and air at the end face of the glass. In this instance, a glass pane which is similarly shaped as glass pane 31 shown in FIG. 9 is cut by a plane corresponding to first reflecting surface 30a to split the glass pane into a pair of glass panes 41a, 41b having respective cut surfaces 40a, 40b, which are assembled together with a spacing $d_3$ therebetween. The cut surface 40b of glass pane 41b functions as the first reflecting surface. Glass pane 41b is formed with second reflecting surface 30b which is similar to that shown in FIG.9. Consequently, first reflecting surface 40b is disposed at a large angle of inclination with respect to the optical axis of light guide 6 and in opposing relationship with second reflecting surface 30b.

In this embodiment, illuminating light $L_1$ which impinges upon reflecting surface 40b in parallel relationship with the optical axis of light guide 6 is reflected toward second reflecting surface in the same manner as illustrated in FIG. 9 to provide an illuminating light. However, an illuminating light which impinges on reflecting surface 40b with an angle of incidence less than the critical angle of glass pane 41b is permitted to transmit through reflecting surface 40b while preventing it from being reflected toward light guide 6, as indicated by dotted lines, thus directing it through glass panes 41a and 22 to provide an effective illuminating light. With this embodiment, an area to be observed can be illuminated with a brightness level which is higher than that available with the embodiment shown in FIG. 9.

In the embodiments described above, light guide 6 is disposed close to a reflecting surface or surfaces, but it should be understood that light guide 6 may be replaced by a light source such as a lamp, light emitting diode or the like.

What is claimed is:

1. In an endoscope, the combination comprising:
   (A) an observation optical system having an observation optical axis and terminating in an observation window, said observation optical axis extending through said observation window;
   (B) a source of illuminating light; and
   (C) an illumination optical system including a refractive element and first and second reflecting surfaces, said illumination optical system being positioned at a location which causes:
      (1) a first portion of said illuminating light to pass through said refractive element on both sides of said first reflecting surface and to be transmitted through said illumination optical system along a first optical axis which is oblique to said observation optical axis and crosses said observation optical axis at a first point located in front of said observation window; and
      (2) a second portion of said illuminating light to reflect off said first and second reflecting surfaces and to be transmitted through said illumination optical system along a second optical axis which is oblique to said observation optical axis and crosses said observation optical axis at a second point located in front of said observation window, said first point being further from said observation window than said second point as measured along said observation optical axis whereby said first portion of illuminating light serves primarily to illuminate objects which are relatively far from said observation window and said second portion of illuminating light serves primarily to illuminate objects which are relatively close to said observation window.

2. In an endoscope, the combination according to claim 1, wherein said first reflecting surface is located along said first optical axis.

3. In an endoscope, the combination according to claim 2, wherein said first reflecting surface is angled to reflect said second portion of said illuminating light in a direction away from said observation optical axis and said second reflecting surface is positioned to receive illuminating light reflected off said first reflecting surface and to reflect said received light in a direction towards said observation optical axis.

4. In an endoscope, the combination according to claim 3, wherein said second reflecting surface is formed by a curved surface which condenses the reflected light received thereby.

5. In an endoscope, the combination according to either one of claims 3 or 4, wherein said refractive element comprises first and second transparent panes and wherein said first reflective surface is defined by a space located between said panes.

6. In an endoscope, the combination according to claim 5, wherein the angle of said reflective surface is such that some of said illuminating light impinging on said first reflective surface is reflected towards said second reflective surface and some of said illuminating light impinging on said first reflective surface is refracted in the direction of said observation optical axis.

7. In an endoscope, the combination according to claim 5 in which a concave lens is disposed between said source and said first reflecting surface.

8. In an endoscope, the combination according to claim 5 in which said source comprises a light guide.

9. In an endoscope, the combination according to claim 5, wherein said refractive element is made of a transparent material and said first reflective surface is integrally formed therewith.

10. In an endoscope, the combination according to claim 5, wherein said refractive element comprises first and second adjacent panes of transparent material and wherein said first and second reflective surfaces are formed in or on at least one of said panes.

11. In an endoscope, the combination according to any one of claims 1, 2, 3 or 4, wherein a concave lens is disposed between said source of illuminating light and said first reflecting surface.

12. In an endoscope, the combination according to claim 11 in which said source comprises a light guide.

13. In an endoscope, the combination according to claim 11, wherein said refractive element is made of a transparent material and said first reflective surface is integrally formed therewith.

14. In an endoscope, the combination according to claim 11, wherein said refractive element comprises first and second adjacent panes of transparent material and wherein said first and second reflective surfaces are formed in or on at least one of said panes.

15. In an endoscope, the combination according to any one of claims 1, 2, 3 or 4, wherein said source of illuminating light comprises a light guide.

16. In an endoscope, the combination according to any one of claims 1, 2, 3 or 4, wherein said refractive element is made of a transparent material and said first reflective surface is integrally formed therewith.

17. In an endoscope, the combination according to any one of claims 1, 2, 3 or 4, wherein said refractive element comprises first and second adjacent panes of transparent material and wherein said first and second reflective surfaces are formed in or on at least one of said panes.

* * * * *